Figure 1:
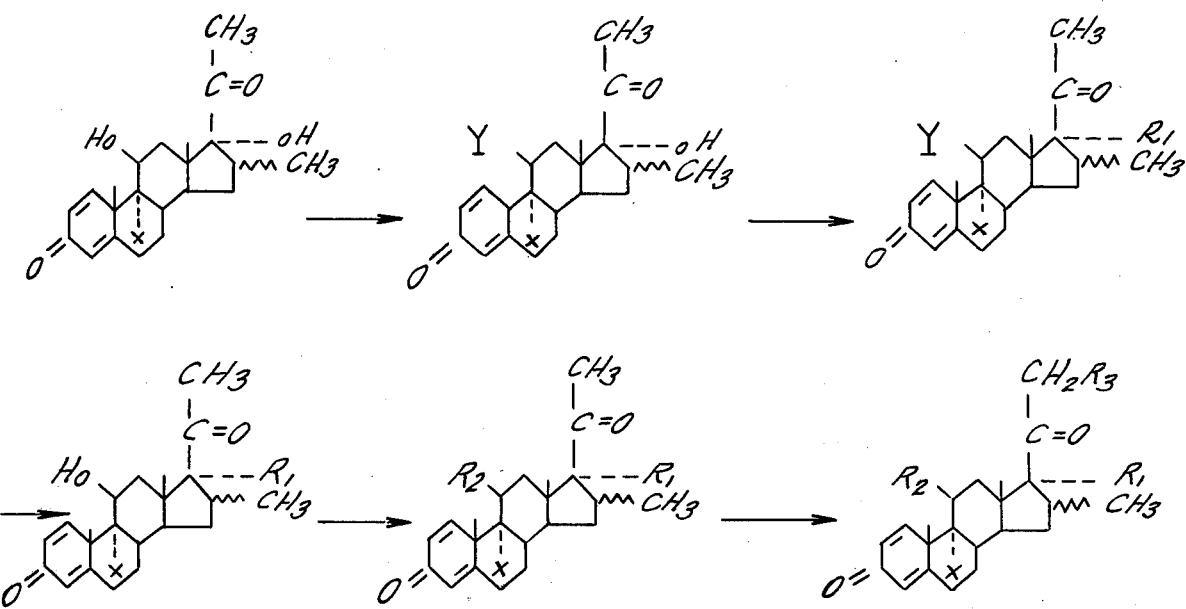
Figure 2:
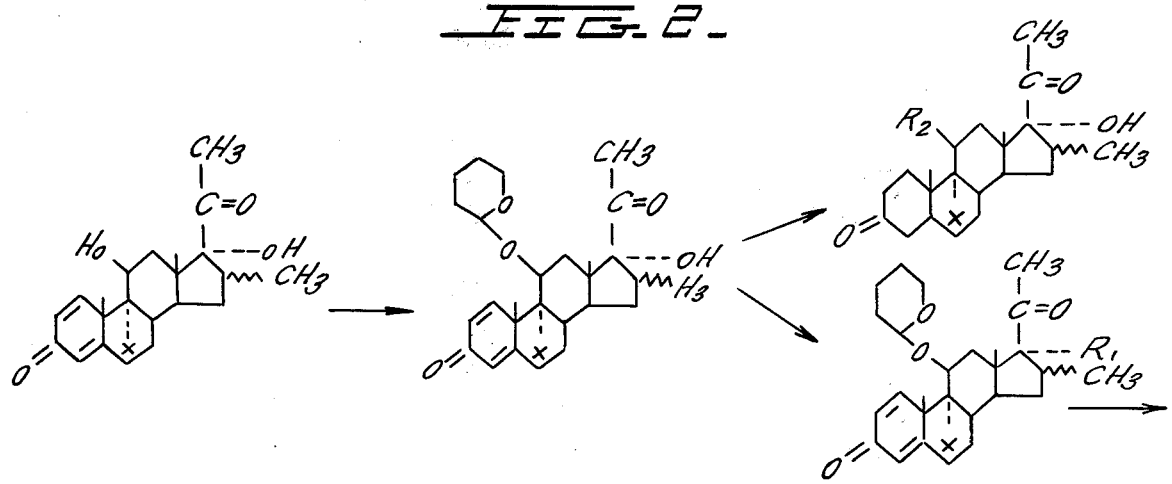
Figure 2:
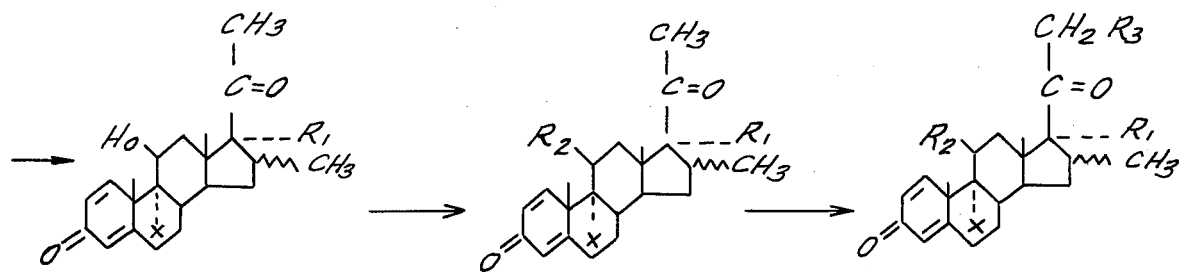
Figure 3:
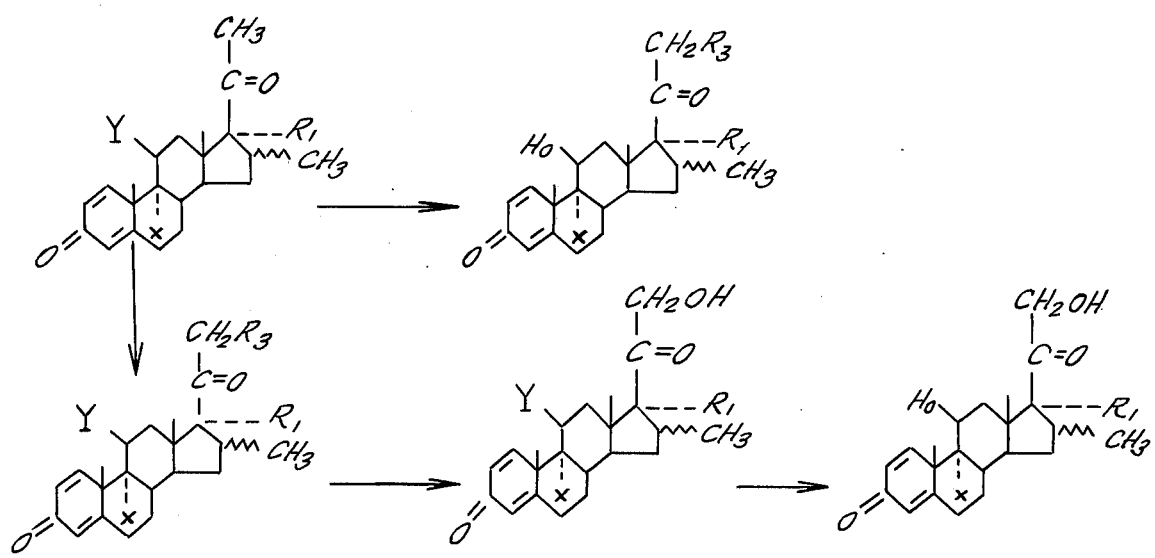
Figure 4:
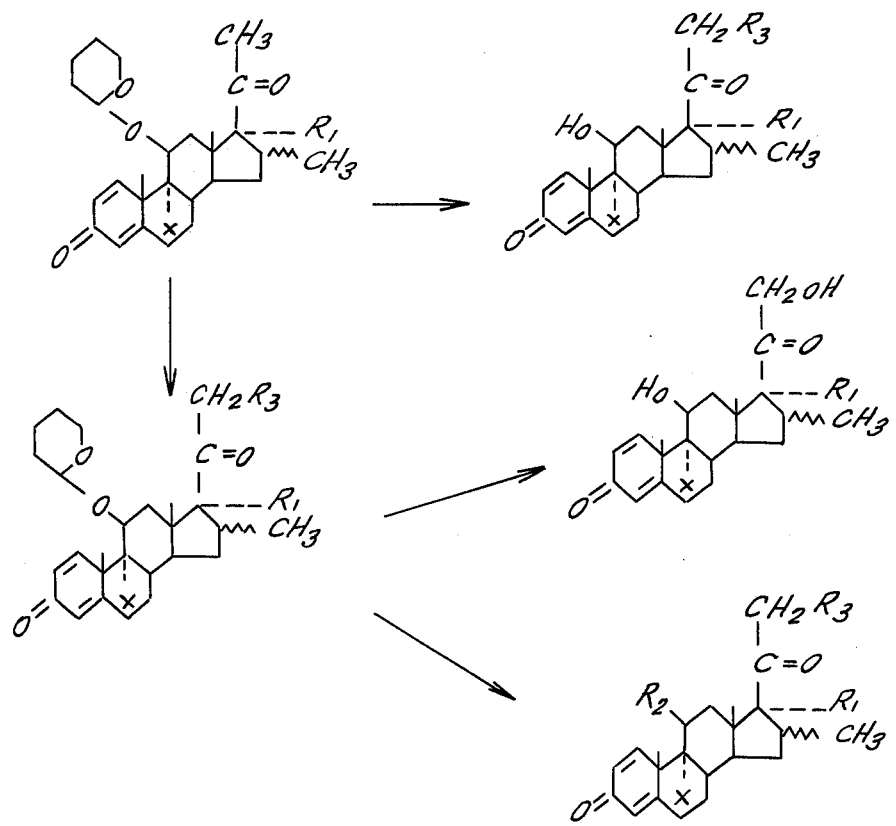

United States Patent [19]

Villax

[11] 4,024,131
[45] May 17, 1977

[54] 16-METHYL-9α-HALO STEROID ESTERS, ETHERS AND PREPARATION THEREOF

[75] Inventor: Joao Emerico Villax, Lisbon, Portugal

[73] Assignee: Plurichemie Anstalt, Vaduz, Liechtenstein

[22] Filed: Mar. 25, 1975

[21] Appl. No.: 561,948

[30] Foreign Application Priority Data

Mar. 27, 1974 Portugal .............................. 61636
Mar. 27, 1974 Portugal .............................. 61637

[52] U.S. Cl. .................. 260/239.55 R; 260/397.45
[51] Int. Cl. ......................... C07j 5/00; C07j 17/00
[58] Field of Search ............................ 260/397.45

[56] References Cited

UNITED STATES PATENTS

| | | | |
|---|---|---|---|
| 3,444,217 | 5/1969 | Shapiro et al. | 260/397.45 |
| 3,557,162 | 1/1971 | Lens et al. | 260/397.45 |
| 3,639,434 | 2/1972 | Oxley et al. | 424/243 |
| 3,652,554 | 3/1972 | Anner et al. | 260/239.55 |
| 3,764,616 | 10/1973 | Elks et al. | 260/397.45 |

Primary Examiner—Elbert L. Roberts
Attorney, Agent, or Firm—Ostrolenk, Faber, Gerb & Soffen

[57] ABSTRACT

New 16-methyl-9α-halo corticosteroid esters and ethers having high topical anti-inflammatory potency and low systemic activity and the manner in which they can be produced are described.

30 Claims, 4 Drawing Figures

16-METHYL-9α-HALO STEROID ESTERS, ETHERS AND PREPARATION THEREOF

The topical application of steroid compounds is today of great importance, and considerable work has been done so as to prepare steroids with greater anti-inflammatory potency.

The present invention is primarily concerned with the preparation of new 16-methyl-9α-halo corticosteroid esters and ethers having a high topical anti-inflammatory potency and the lowest possible systemic activity. These new compounds have a higher ratio of topical anti-inflammatory potency/systemic activity than any of the hitherto described topical anti-inflammatory steroids. A further object of the present invention is to provide new esters of 16-methyl-9α-halo corticosteroids having an outstanding protracted activity when administered parenterally.

The present invention also provides a process which permits one to obtain 17α-mono and 11β,17α-diesters of the 21-desoxyprednisolones, more specifically those of 16α and 16β-methyl-9α-fluoro or 9α-chloro-21-desoxyprednisolone, which were not hitherto described, as well as 17α-monoesters, 11β,17α and 17α,21-diesters, and 11β,17α,21-triesters of 16α or 16β-methyl-9α-fluoro or 9α-chloro-prednisolone, in uniform and high yields, with practically no limitation or restriction. The process has the special feature that the carbon atoms of the ester groups are not limited to a low number and satisfactory yields are obtained between 1 to 16 carbon atoms per each ester group.

Consequently, the present process also permits one to obtain 17α-monoesters of 16α and 16β-methyl-9α-fluoro or 9α-chloro-21-desoxyprednisolone, wherein the esterifying carboxylic acid has more than 4 carbon atoms, which until now were not obtainable by the known processes.

Accordingly, it is an object of the invention to provide new steroid compounds of the general formula:

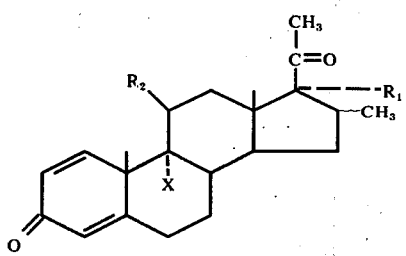

(I)

where $R_1$ is an esterified hydroxy group of 1 to 16 carbon atoms, $R_2$ is a hydroxy or an esterified hydroxy group of 1 to 18 carbon atoms or a tetrahydropyran-2′yloxy, when X is chlorine; and $R_1$ is an esterified hydroxy group of 5 to 16 carbon atoms, $R_2$ is a hydroxy or an esterified hydroxy group of 1 to 8 carbon atoms or a tetrahydropyran-2′yloxy, when X is fluorine. The methyl group at C 16 can either be at the α or β position.

Among these new steroids, the 17α-monoesters having 5 to 7 carbon atoms in the ester grouping exert the highest local anti-inflammatory potency when administered topically and the lowest systemic activity, especially when X is chlorine. The preferred 11β,17α-diesters for topical use are those where the total number of carbon atoms in two ester groups does not exceed 10 and lies preferably between 6 and 8. Further, these 9α-chlorinated steroid esters have the advantage that their application will not cause skin atrophy.

In these pharmaceutically useful new compounds, the esterifying acids at 11β and/or 17α are chosen from pharmaceutically acceptable saturated or unsaturated straight, branched aliphatic, cycloaliphatic, aromatic, heterocyclic carboxylic acids, whether substituted or not. $R_1$ and $R_2$ can be the same or different substituents. It is well known that when the number of carbon atoms in the 17-esterified hydroxy group exceeds 7, the topical activity drops dramatically. It has now been found that the new compounds of formula I, when the 17α-ester group contains between 8 and 16 carbon atoms and 11β is a hydroxy or an esterified hydroxy group of 1 to 8 carbon atoms, exert a prolonged anti-inflammatory activity when administered intramuscularly. The preferred compounds are those which contain from 7 to 10 carbon atoms in $R_1$, and the total number of carbon atoms among the 17α-monoesters and among the 11β,17α-diesters is preferably from 8 to 12.

The 16-methyl-9α-fluoro or 9α-chloro-21-desoxy 11β and/or 17α-mono and diesters are also valuable intermediates for preparing pharmaceutically useful anti-inflammatory compounds.

Accordingly, a further object of the present invention is to prepare the new compounds of the formula:

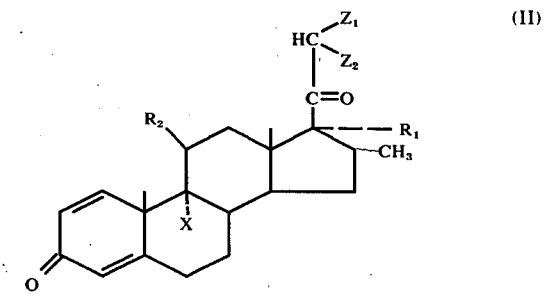

(II)

where $Z_1$ is iodine, $Z_2$ is hydrogen or iodine, $R_1$ is an esterified hydroxy group of 1 to 16 carbon atoms and $R_2$ is a hydroxy or an esterified hydroxy group of 1 to 8 carbon atoms or a tetrahydropyran-2′yloxy group.

Furthermore, the invention provides, through acylation of the compounds of the formula II, compounds of the formula:

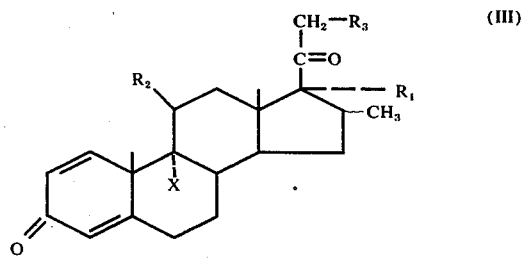

(III)

where $R_1$, $R_2$ and X have the same meaning as above and $R_3$ has the same meaning as $R_1$ or can be either an o-phosphoryloxy or sulphuryloxy group.

It has been found that the new 11β,17α,21-triesters, having a total of 3 to 11 carbon atoms in the three ester functions, exert a high anti-inflammatory potency and are of a very low systemic activity when administered topically, especially those containing a chlorine atom, and when the total number of carbon atoms in the ester groupings is above 11, the new triesters exert a protracted activity when administered parenterally, especially those containing a fluorine atom.

Finally, the invention also provides new selective processes of solvolysis and/or hydrolysis to prepare 17α-monoesters, 11β,17α and 17α,21-diesters.

According to the invention, the preferred new compounds are, among others:

A. For topical use

16β-methyl-9α-chloro-21-desoxyprednisolone 17α-propionate, butyrate, isobutyrate and valerate, 16β-methyl-9α-fluoro-21-desoxyprednisolone 17α-valerate, 16β-methyl-9α-chloro-21-desoxyprednisolone 17α-benzoate, 16β-methyl-9α-chloro-21-desoxyprednisolone 11β,17α-dipropionate, 16β-methyl-9α-fluoro-21-desoxyprednisolone 11β-propionate 17α-valerate, 16β-methyl-9α-chloro-21-desoxyprednisolone 11β-benzoate 17α-propionate, 16β-methyl-9α-chloro and 9α-fluoroprednisolone 11β,21-diacetate 17α-propionate, 16β-methyl-9α-chloro and 9α-fluoroprednisolone 11β,17α-dipropionate 21-acetate, 16β-methyl-9α-chloro and 9α-fluoroprednisolone 11β,17α,21-tripropionate, 16β-methyl-9α-chloro and 9α-fluoroprednisolone 11β-propionate 17α-valerate 21-acetate.

All these preferred compounds have a high anti-inflammatory potency and very low systemic activity when applied locally and their ratio is more favorable than any of the hitherto described anti-inflammatory topical steroids.

B. For protracted activity when administered intramuscularly

16β-methyl-9α-fluoro-21-desoxyprednisolone 17α-heptanoate,

16β-methyl-9α-fluoro-21-desoxyprednisolone 17α-diethylpropionate,

16β-methyl-9α-fluoro-21-desoxyprednisolone 11β-propionate 17α-heptanoate,

16β-methyl-9α-fluoroprednisolone 11β-propionate 17α-heptanoate,

16β-methyl-9α-fluoroprednisolone 11β-21-dipropionate 17α-valerate,

16β-methyl-9α-fluoroprednisolone 11β,17α,21-tripropionate.

These preferred compounds are characterized by a depot effect when administered intramuscularly and provide clinically useful maintenance levels during a long period of time, 2 to 12 days according to the dosage and the vehicle of administration, in patients where a long cortisone therapy is indicated. Thus, the frequency of administration is diminished and the secondary effects, such as gastric hemorrhagies which may occur on prolonged oral therapy, are avoided.

Naturally, the equivalent 16α-methyl analogs are a part of the preferred compounds.

The common starting compound in the 16β-methyl-9α-fluorinated series is 16β-methyl-9α-fluoro-11β,17α-dihydroxy-1,4-pregnadiene-3,20-dione, the synthesis of which was first described in applicant's U.S. Pat. No. 3,792,046. The 9α-chloro analog is easily obtained from 16β-methyl-9(11)-epoxy-17α-hydroxy-1,4-pregnadiene-3,20-dione, a compound which is claimed in the same patent, by contacting it with aqueous concentrated hydrochloric acid.

The analogous starting compounds in the 16α-methyl series are described in Britsh Pat. No. 934,701.

These starting 21-desoxy steroids have two hydroxy groups, namely at the 11β and 17α-position.

In the prior art (British Pat. No. 1,070,751), the 17α-hydroxy group of 16α or 16β-methyl-9α-fluoro-21-desoxyprednisolone is directly esterified under acid conditions by methods known per se. However, the selectivity of esterification is insufficient according to this prior art, and the 11β-hydroxy group is concomitantly esterified, although more slowly. Consequently, yields are low (16–50%), and purification is not easily achieved due to the difficult separation of the 17α-monoester from the 11β,17α-diester. Finally, this prior art process is limited to lower aliphatic acids having a maximum of 4 carbon atoms. In order to avoid these disadvantages, the 11β-hydroxy group is first protected, in accordance with the present invention, with an easily removable group. Such easily removable protecting groups are di-, trichloro or fluoroacetates, the use of which has been described in steroid chemistry by A. Lardon and T. Reichstein, Helv. Chim. Acta, Vol. 37, p. 388 and 443 (1954).

It has been found that di-, trichloro or fluoroacetic anhydride, preferably trifluoroacetic anhydride, react selectively with the 11β-hydroxy group of 16α or 16β-methyl-9α-chloro or 9α-fluoro-21-desoxyprednisolone, without reacting with the other functional groups in the molecule, yielding the respective 11β-trifluoroacetate.

Another effective way of selective protection of the 11β-hydroxy group is achieved by reacting the 16α or 16β-methyl-9α-fluoro or 9α-chloro-21-desoxyprednisolone with 2,3-dihydropyran in the presence of an acid catalyst.

This protection of primary and secondary alcohols has been described by R. Paul, Bull. Soc. 1, p. 971 (1934).

In order to protect the 11β-hydroxy function, the respective 21-desoxy steroid is reacted with di-, trichloro or fluoroacetic anhydride in presence of pyridine as basic catalyst, either mixed with a reaction inert solvent, such as dioxan or tetrahydrofuran, or with no solvent at all; an excess of the haloacetic anhydride and pyridine will act simultaneously as solvent. The reaction temperature is not critical and can be between −15° C. and the boiling point of the reaction mixture. However, a temperature around 0° C. to room temperature is the preferred range.

The expression di-, trichloro or fluoroacetic anhydride includes mixed haloacetic anhydrides too, such as monofluoro dichloracetic anhydride, etc.

The 17α-hydroxy function of the protected compound I can easily be esterified by any carboxylic acid containing up to 16 carbon atoms, using para-toluenesulfonic acid or perchloric acid as catalyst by methods known per se. This esterification is carried out by using the free acid mixed with trifluoroacetic anhydride, an acid anhydride or a mixed acid anhydride, in presence of an acid catalyst such as perchloric acid or para-toluenesulfonic acid. The acylation agent in a great excess can act simultaneously as solvent, but any reaction inert solvent may also be used. The reaction temperature may range from −15° C. up to the boiling point of the reaction mixture. The preferred way of esterification of the 17α-hydroxy is by reacting a mixture of trifluoroacetic anhydride and the respective carboxylic acid in excess, with or without a reaction inert solvent, the temperature range being between −10° and +5° C. The reaction time is between a few minutes and 2 hours, depending on the reaction temperature.

The protection of the 11β-hydroxy by formation of the 11β-ether blocking is realized at a temperature between 0° and +80° C., using 2,3-dihydropyran in excess which acts simultaneously as solvent, the preferred acid catalyst being phosphorous oxychloride or anhydrous hydrogen chloride in dioxan. The addition of a slight amount of dimethylsulfoxide or dimethylformamide will complete the dissolution of the product. The reaction is completed between 1 to 40 hours.

Once the 11β-hydroxy is protected, the introduction of an ester group in the 17α-position does not present difficulties by methods known per se, such as by acylating the respective acid anhydride in the presence of an acid catalyst such as para-toluenesulfonic acid and perchloric acid, etc., the preferred process being, however, by esterifying with a mixture of the respective acid and trifluoroacetic anhydride.

The 11β-trifluoroacetate protecting group is easily and selectively removed from the 11β,17α-diesters of the 21-desoxy series by hydrolyzing it with a 5% aqueous sodium bicarbonate solution in methanol, without affecting the 17α-ester group. This hydrolysis is completed in about 30 minutes at room temperature. In this manner, the 17α-monoesters of the 21-desoxy series are prepared with yields of 80 to 95%. The 17α-monoesters, thus obtained, can be reesterified at 11β by a carboxylic acid under strongly acid conditions, as known, the process being the same as for the 17-esterification.

Naturally, the 11β-trifluoroacetate 17α-esters of the 21-desoxy series can also be isolated without removing the protecting group at 11β, and the 11β-trifluoroacetate can be subsequently solvolysed in a second step by alkali or earth alkali acetate, carbonate, azide, etc., in methanol or ethanol, as described in British Pat. No. 1,097,164 for the 11β,17α,21-triesters of the pregnane series.

When the 11β-hydroxy is protected through reaction with 2,3-dihydropyran, the 17α-hydroxy group of the thus formed ether can be esterified in the same way as the 11β-trifluoroacetate. The cleavage of the ether group at 11β can be easily achieved in methanol or ethanol 95% containing para-toluenesulfonic acid, or with a diluted aqueous acid or an aqueous solution of magnesium sulfate, reforming the 11β-hydroxy group without affecting the 17α-ester group. Another advantage of this protection is that refluxing the 11β-ether, eventually after esterification of the 17α-hydroxy, in a lower aliphatic carboxylic acid will yield directly the respective 11β-ester or 11β,17α-diester.

Thus, the above process permits one to obtain the 11β and 17α-mono and 11β,17α-diesters of the 21-desoxy steroids with practically no limitation other than the esterification by carboxylic acids having more than 16 carbon atoms is too slow. However, these esters which have more than 16 carbon atoms are devoid of pharmaceutical interest.

According to the present invention, a 21-esterified hydroxy group can be introduced in the 17α-mono and 11β,17α-diesters thus obtained. It has been found that the per se known 21-hydroxylation via the 21-mono or 21,21-diiodo derivatives may successfully be carried out without hydrolyzing the ester group at the 17α or 11β-position. The 21-mono or diiodo derivatives are prepared, as known in the art, by reacting the 11β,17α-mono or diesters of the 21-desoxy steroids with iodine in methanol eventually mixed with tetrahydrofuran, in presence of an alkali, such as calcium oxide, and in absence of water, yielding the 21-monoiodinated derivative; when the reaction mixture contains calcium chloride, the respective 21-diiodo derivative is formed. The mono or diiodo derivatives are subsequently reacted with an alkali metal salt or with an amine salt of a carboxylic acid or of phosphoric or sulfuric acid, yielding the respective 21-hydroxylated derivative under esterified form.

In case the compound to be iodinated has an 11β-di-, trichloro or fluoroacetoxy group, the conditions of iodination and subsequent acyloxylation can be chosen in such a way that this protective group remains in the molecule, or alternatively it is eliminated:

if the precipitation is carried out by adding the reaction mixture very slowly to iced water having a volume of about 10 times the volume of the reaction mixture, no appreciable hydrolysis will occur at 11β;

however, when the precipitating water is added slowly to the reaction mixture, taking 1 to 2 hours, the 11β-protecting group will be completely hydrolyzed without hydrolyzing the 17α and 21-ester groups.

Thus, the 21-acyloxylation provides, in high and uniform yield, the 17α,21-diesters and 11β,17α,21-triesters of 16α or 16β-methyl-9α-fluoro or 9α-chloro-prednisolone, where all ester groupings can be different from each other. Furthermore, it also provides the 11β-di-, trichloro or fluoroacetoxy-17α,21-triesters according to the specific conditions outlined above. It has been found that these 11β-di-, trichloro or fluoro esters can be selectively hydrolyzed at 21 using perchloric acid (60–70%) in methanol to yield the 11β-di, trichloro or fluoro 17α-diesters. The reaction temperature is between 0° C. and room temperature and the time of reaction is 12 to 24 hours. However, when using a weak alkaline hydrolysis, the 11β-di-, trichloro or fluoroacetyl group can be selectively removed without affecting the 17α and 21-ester functions. Such selective hydrolysis is carried out by adding 0.35 to 1.0 mol of a diluted aqueous sodium bicarbonate solution to each mole of the triester in methanol, under stirring for 0.5 to 1.5 hours at room temperature. After acidification with 0.5 N acetic acid and precipitation with water, the 17α-21-diesters are obtained in a nearly quantitative yield.

In contrast to the above observation, treatment of 11β-tetrahydropyranyloxy 17α,21-diester with perchloric acid in methanol as above, followed by the slow addition of water, will precipitate the respective 17α-monoester as the 11β-tetrahydropyranyloxy group is much more sensitive to acid conditions than the 11β-fluoroacetate. However, the 11β-tetrahydropyranyloxy group will not undergo cleavage in lower carboxylic acids such as acetic acid and propionic acid at room temperature.

Furthermore, it has been found that the 11β-di, trichloro or fluoroacetoxy group can be selectively solvolysed starting from the respective 11β,17α-diesters of the 21-desoxy and 21-hydroxy series, as well as from the respective 11β, 17α,21-triesters, without solvolysing the other ester functions present. The solvolysis is carried out in a suitable organic solvent, such as di-, tri-, tetrachloromethane, tetrahydrofuran, dioxan, benzene, ethylacetate or mixtures thereof, by catalytic action of activated silicic acid, i.e., silica gel. However, to assure good yields, a few conditions have to be satisfied. The silica gel should preferably be activated at 110° C. A preferred way of carrying out this activation is as follows:

A water saturated silica gel is dried by heating to a temperature of 110° C. for 1 to 2 hours. The solvolysis yield may vary as much as from 3 to 100%, depending on the origin and grade of the silica gel as well as on its activation. Good yields may be obtained using "Silica Gel for TLC" of "Camag", Muttern (Switerzerland) — quality which contains 20% water — after activation for 1 hour at 110° C. The silica gel is present in a considerable excess and it is contacted with the solution of the compound to be solvolysed between 1 to 12 hours. The solvolysis can be carried out either by passing the organic solution slowly through a chromatographic column or by simply stirring the organic solution with the silica, followed by filtration. The optimum time of solvolysis should be determined by thin-layer chromatography in the course of the reaction, as this may vary considerably according to the quality and degree of activation of the silica gel and the compound to be solvolysed. It should be noted that prolongation of the time of contact over the optimum is detrimental and yields will decrease. The silica gel, which absorbs the steroid completely, is then dried at a low temperature between 25° and 45° C. and eluted with a suitable solvent mixture, such as 1:1 chloroform and methanol. However, other solvent mixtures maybe useful, depending on the substituents present in the molecule. The eluate is subsequently evaporated under reduced pressure and recrystallized. The silica gel catalyzed solvolysis is also applicable to the solvolysis of the 11β-propanyloxy group under the same conditions as for the 11β-di, trichloro or fluoroacetates, the yield being above 90%.

The solvolysis of tritylethers catalyzed by activated silica gel has been described by J. Lehrfeld, Journ. Org. Chem., Vol. 32, p. 2544–6 (1967).

All the mono, di and triesters herein described are little soluble in water. Therefore, they can be isolated through precipitation by adding water to the reaction mixture. The crude esters are subsequently purified by methods known in the art. The Examples appearing hereinafter illustrate the various ways of isolation and purification.

The process of the present invention is summarized in the reaction sequences in the four Figures which represent pathways, I, II, III and IV, respectively. In the Figures, Y represents di-, trichloro or fluoroacetoxy.

It is evident that the process herein described, besides yielding the new pharmaceutically useful steroid compounds, also permits one to obtain with high yields and in a simple manner the known 17α-monoesters and 17α,21-diesters of 16α and 16β-methyl-9α-fluoro or chloro-prednisolone. The preparation of these esters is described in British Pat. Nos. 996,080, 1,043,518, 1,047,519 and in U.S. Pat. No. 3,529,060. All these inventions make use of an esterification via 17α,21-(1¹-alkoxy)-1¹-substituted methylene dioxy steroids (17α,21-cyclic orthoesters) which are subsequently hydrolyzed in acid conditions to yield the corresponding 17α-acylates. British Pat. No. 1,047,519 describes the preparation of the 17α,21-diesters by acylating the 21-hydroxy 17α-monoesters under alkaline conditions by processes known per se. It is to be noted that this British patent also claims the direct esterification of the 17α-hydroxy group of the 21-esters of 11β,17α,21-trihydroxy steroid compounds. The sole example 25 demonstrates that this process is devoid of practical interest due to the formation of mixtures of 11β,17α,21-triacetate, 11β,21-diacetate and 17α,21-diacetate. The desired 17α,21-diacetate was not obtained in pure form even after preparative chromatographic column separation and its presence could only be demonstrated by thin-layer chromatography. Consequently, all these processes first prepared the cyclic orthoesters, using the reagent, the respective orthoesters which are not commercially available and the preparation of which is complicated and limited to the lower alkyl chains up to 9 carbon atoms.

The pharmaceutically useful new compounds of the present invention can be mixed with a suitable carrier for the preparation of lotions, ointments, creams, other topical formulations, including sprays for inhalation, and injections for intraarticular and intramuscular administration in the know manner.

EXAMPLE 1

PREPARATION OF 16α AND 16β-METHYL-9α-CHLORO-11β,17α-DIHYDROXY-1,4-PREGNADIENE-3,20-DIONE (16α AND 16β-METHYL-9β-CHLORO-21-DESOXYPREDNISOLONES)

25 g of 16β-methyl-9(11)-epoxy-17-hydroxy-1,4-pregnadiene-3,20-dione, obtained according to example 2 of U.S. Pat. No. 3,792,046, is dissolved in 500 ml of concentrated hydrochloric acid at room temperature, taking about 5 to 6 minutes. Subsequently, 500 ml of water is added and after stirring the reaction mixture, the desired product crystallizes. After stirring for 4 hours, 1250 ml of water is added and neutralized with 25% ammonia, provoking crystallization of the 16β-isomer of the title compound. Yield 24.9 g. Melting point 208°–218° C. Recrystallization from acetone yields the pure product. Melting point 225°–232° C. $E_1^{1\%}{}_{cm}$ 392 at 239 mμ in methanol. The main peaks of the infrared absorption in mineral oil mull are at 2.9 μ, 5.82 μ, 6.0 μ, 6.14 μ, 6.21 μ, 9.55 μ, 11.28 μ. $/\alpha/_D^{22}$ −118±5 (c=1, in dioxan).

The respective 16α-methyl-9α-chloro-21-desoxyprednisolone is prepared in the same manner, starting from the respective 9(11)-epoxide described in stage 10 of example 1 of British Pat. No. 934,701. Yield 25.2g. Melting point 255°–262° C. with decomposition.

EXAMPLE 2

17α-MONO AND 11β,17α-DIESTERS OF 16α AND 16β-METHYL-9α-CHLORO-21-DESOXYPREDNISOLONES

Stage a — 20 g of the 16β-methyl isomer obtained in Example 1 is dissolved in 50 ml of pyridine and this solution is added, under stirring, to 50 ml of pyridine containing 12 ml of trifluoroacetic anhydride at −10° C. Stirring is continued for 45 minutes at 0° C. and the reaction mixture is poured into 4 liters of iced water. Yield 24.1 g of 16β-methyl-9α-chloro-11β,17α-dihydroxy-1,4-pregnadiene-3,20-dione 11β-trifluoroacetate.

The main peaks of the infrared absorption in mineral oil mull are at 2.9 μ, 5.6 μ, 5.83 μ, 5.99 μ, 6.11 μ, 6.18 μ, 11.22 μ, 12.29 μ.

Stage b — 20 g of the crude product obtained in stage a is added to a mixture of 200 ml of n-valeric acid and 80 ml of trifluoroacetic anhydride. It is heated to 80° C. for 2.5 hours. Subsequently, the reaction mixture is poured into 2400 ml of hot water and is heated to 100° C. until the excess of acid anhydride decomposes. The diluted reaction mixture is then extracted three times with 250 ml of dichloromethane and the reunited organic phases are washed twice with water and with water containing 1% pyridine, and again with water. The organic phase is dried with magnesium sulfate and filtered, and the filtrate is evaporated to dryness in vacuum. The solids are then dissolved in the minimum amount of pyridine necessary and reprecipitated with iced water, and the pyridine is neutralized with diluted hydrochloric acid, yielding 18.1 g of 16β-methyl-9α-chloro-11β,17α-dihydroxy-1,4-pregnadiene-3,20-dione 11β-trifluoroacetate 17α-valerate. The main peaks of the infrared absorption in mineral oil mull are at 5.58 $\mu$, 5.77 $\mu$ (broad), 5.98 $\mu$, 6.1 $\mu$, 6.2 $\mu$, 8.12 $\mu$, 11.22 $\mu$, 12.32 $\mu$(broad). There are no peaks in the region of 2.5 to 3 $\mu$.

The respective 16α-methyl isomer is obtained in a similar manner.

Stage c — 10 g of the 16β-methyl isomer of the previous stage in 80 ml of methanol is made slightly alkaline by adding 5% aqueous solution of sodium bicarbonate (5–10% excess). After standing for 30 minutes at room temperature, it is acidified with 5 N acetic acid and precipitated by adding 500 ml of iced water. It is filtered, washed with water and dried, yielding 7.9 g of 16β-methyl-9α-chloro-21-desoxyprednisolone 17α-valerate. The main peaks of the infrared absorption in mineral oil mull are at 3.0 $\mu$, 5.78 $\mu$, 6.0 $\mu$, 6.15 $\mu$, 6.21 $\mu$, 11.24 $\mu$, 12.35–12.40 $\mu$.

Alternatively, 1 g of the product obtained in stage b is dissolved in 220 ml of chloroform and mixed with silica gel (Silica Gel "Camag", Muttern, Switerzerland, containing 20% water), activated at 110° C, for 1 hour and stirred. An aliquot is taken every hour, than it is filtered, washed with a small amount of chloroform and eluated with 1 ml of a mixture of chloroform and methanol (1:1). The eluate is controlled by thin-layer chromatography. After 10 hours, the spot of the diester is no longer visible on the thin-layer chromatography plate (coating silica gel Merck 254; mobile phase 95 parts of dichloroethane, 5 parts of methanol and 0.2 parts of water. The spots are revealed by spraying with 50% orthophosphoric acid and heated to 180° C. for 5 minutes). Subsequently, the reaction mixture is filtered and washed with chloroform. The silica gel is extracted with 120, 60 and 60 ml of chloroform and methanol (1:1). The eluates are concentrated to dryness, dissolved in 10 ml of acetone, precipitated by addition of 200 ml of water and ice, filtered, washed and dried. The product is recrystallized from acetone and hexane, yielding the desired 16β-methyl-9α-chloro-21-desoxyprednisolone 17α-valerate, identical to the product obtained above by hydrolysis.

Stage d — 10 g of 16β-methyl-9α-chloro-11β,17α-dihydroxy-1,4-pregnadiene-3,20-dione 17α valerate, obtained according to the process in the previous stage, is esterified at the 11β-hydroxy in 200 ml of propionic acid mixed with 80 ml of trifluoroacetic anhydride, using the process in stage b for esterification of the 17α-hydroxy group, yielding 22.2 g of the respective 11β-propionate 17α-valerate.

In an analogous manner, the following 17α-monoesters are obtained through hydrolysis or solvolysis of the respective 11β-trifluoroacetates:

16αor 16β-methyl-9α-chloro-21-desoxyprednisolone:
17α-acetate
17α-propionate
17α-butyrate
17α-isobutyrate
17α-trimethylacetate
17α-heptanoate
17α-benzoate
17α-isonicotinate as well as the 11β,17α-diesters of:

16α or 16β-methyl-9α-chloro-21-desoxyprendnisolone:
11β,17α-diacetate
11β,17α-dipropionate
11β,17α-dibutyrate
11β,17α-divalerate
11β-propionate 17α-valerate
11β-propionate 17α-heptanoate
11β-propionate 17α-benzoate
11β-propionate 17α-isonicotinate
11β-benzoate 17α-propionate

EXAMPLE 3

17α-MONO AND 11β,17α-DIESTERS OF 16α AND 16β-METHYL-9α-FLUORO-21-DESOXYPREDNISOLONES

Stage a — 20 g of 16β-methyl-9α-fluoro-11β,17α-dihydroxy-1,4-pregnadiene-3,20-dione, obtained according to example 3 of U.S. Pat. No. 3,792,046, is treated according to stage a of Example 2, to yield the respective trifluoroacetate — 23.9 g. After recrystallization from acetone and hexane, the product melts at 205°–208° C. $E_1^{1\%}{}_{cm}$ 316 at 238 m$\mu$ in methanol. /α/$_D^{22}$ +100 (c=1, in dioxan). The main peaks of the infrared absorption in mineral oil mull are at 2.95 $\mu$, 5.56 $\mu$, 5.81 $\mu$, 5.99 $\mu$, 6.12 $\mu$, 6.2 $\mu$, 8.18 $\mu$, 10.0 $\mu$, 11.08 $\mu$, 11.14 $\mu$, (shoulder), 12.8 $\mu$.

Stage b — 20 g of the product obtained in the previous stage is reacted as described in stage b of Example 2, yielding 16β-methyl-9α-fluoro-11β,17α-dihydroxy-1,4-pregnadiene-3,20-dione 11β-trifluoroacetate 17α-valerate. The main peaks of the infrared absorption in mineral oil mull are at 5.58 $\mu$, 5.75 $\mu$(broad), 5.98 $\mu$, 6.1 $\mu$, 6.2 $\mu$, 8.12 $\mu$, 11.2 $\mu$. There are no peaks in the region of 2.5 to 3 $\mu$.

Stage c — 1 g of the product obtained in the previous stage is hydrolyzed according to the process in stage c of Example 2, yielding 0.8 g of 16β-methyl-9α-fluoro-21-desoxyprednisolone 17α-valerate. The main peaks of the infrared absorption in mineral oil mull are at 2.9 $\mu$, 5.75–5.81 $\mu$, (doublet), 5.99 $\mu$, 6.11 $\mu$, 11.13 $\mu$, 11.5 $\mu$. Melting point 202°–210° C. It is about twice as potent as betamethasone 17α-valerate in McKenzie's vasoconstriction test.

The solvolysis with silica gel in chloroform takes 9 hours. At the end of solvolysis, the spot on the thin-layer chromatographic plate of the 11β-trifluoroacetate 17α-valerate (Rf 0.44) practically disappeared. After working up, a 17α-valerate identical to the compound obtained by hydrolysis is obtained.

Stage d — 10 of 16β-methyl-9α-fluoro-11β,17α-dihydroxy-1,4-pregnadiene-3,20-dione 17α-valerate obtained according to the process in the previous stage is esterified at the 11β-hydroxy as in stage d of Example 2, yielding 21.4 g of the respective 11β-propionate 17α-valerate.

In an analogous manner, the following 17α-monoesters are obtained through hydrolysis or solvolysis of the respective 11-trifluoroacetates:

16α or 16β-methyl-9α-fluoro-21-desoxyprednisolone:
  17α-isovalerate
  17α-trimethylacetate
  17α-heptanoate
  17α-diethylpropionate
  17α-caprylate
  17α-palmitate
  17α-butyrate
  17α-isonicotinate
as well as the 11β,17α-diesters of:

16α or 16β-methyl-9α-fluoro-21-desoxyprednisolone:
  11β-propionate 17α-valerate
  11β-butyrate 17α-valerate
  11β-butyrate 17α-heptanoate
  11β-valerate 17α-heptanoate
  11β-benzoate 17α-propionate 11β-propionate 17α-diethylacetate 11β-propionate 17α-heptanoate
  11β-butyrate 17α-trimethylacetate 11β-propionate 17α-benzoate
  11β-propionate 17α-isonicotinate

EXAMPLE 4

17α,21-DIESTERS OF 16α AND 16β-METHYL-9α-CHLORO-21-PREDNISOLONES

Stage a — 21.3 g of the 11β-trifluoroacetate 17α-valerate, obtained in stage b of Example 2, is added to a mixture of 56 ml of absolute methanol and 14 ml of a 10% methanolic solution of calcium chloride. After stirring for 5 minutes, 7 g of calcium oxide powder is added and stirring is continued for 15 minutes at room temperature. Subsequently, a solution of 18.8 g of resublimed iodine in 42 ml of a 10% methanolic solution of anhydrous calcium chloride and 28 ml of absolute methanol is added to the reaction mixture of the steroid, under nitrogen atmosphere with the exclusion of direct light, at a temperature of 25° to 28° C., in such a way as to maintain a constant discoloration, the addition taking about 40 to 60 minutes. After an additional stirring of 20 minutes, the reaction mixture is cooled to −15° C. and poured into 2000 ml of water containing 500 g of ice and 25 ml of acetic acid. It is stirred for 30 minutes, filtered, washed with water and dried at 30° to 35° C. The 21,21-diiodo derivative, thus obtained, is sufficiently pure to be used in the subsequent reaction step.

Stage b — 27.5 g of the 21,21-diiodo derivative obtained in the previous stage is dissolved in dimethylformamide and this solution is added to a mixture of 210 ml of acetone and 2.1 ml of acetic acid containing 21 g of anhydrous potassium acetate. It is refluxed for 1.5 hours in the dark and under a nitrogen atmosphere. It is then cooled to +10° C. and added to 1200 ml of water containing 300 g of ice and 20 ml of acetic acid. It is filtered and dried, yielding 20.1 g of the desired 16β-methyl-9α-chloro-11β17α,21-trihydroxy-1,4-pregnadiene-3,20-dione 11β-trifluoroacetate 17α-valerate 21-acetate. The main peaks of the infrared absorption in mineral oil mull are at 5.59 $\mu$, 5.19–5.24 $\mu$ (doublet), 5.99 $\mu$, 6.1 $\mu$, 6.18 $\mu$, 8.1 $\mu$, 8.5 $\mu$, 8.7 $\mu$, 11.28 $\mu$. There is no peak in the region of 2.5 to 3.0 $\mu$.

Stage c — 1 g of the product obtained in the previous stage is dissolved in 10 ml of methanol and 1 ml of a 5% aqueous solution of sodium bicarbonate is added at room temperature. After stirring for 1 hour, it is acidified to pH 5 with 0.5 N acetic acid and precipitated with 200 ml of water, yielding 16β-methyl-9α-chloro-11β,17α,21-trihydroxy-1,4-pregnadiene-3,20-dione 17α-valerate 21-acetate. By repeating the same process but using 1 g of 16β-methyl-9α-chloro-prednisolone 11β-trifluoroacetate 17α,21-dipropionate and 2.5 ml of a 5% sodium bicarbonate solution, one obtaines 16β-methyl-9α-chloro-prednisolone 17α,21-dipropionate with a yield of 96.2%.

In an analogous manner, the following 17α,21-diesters are prepared through the respective 11β-trifluoroacetates:

16β or 16β-methyl-9α-chloro-prednisolone:
  17α,21-diacetate
  17α,1-dipropionate
  17α,21-dibutyrate
  17α,21-divalerate
  17α-propionate 21-acetate
  17α-valerate 21-acetate 17α-heptanoate 21-propionate 17α-heptanoate 21-sulfate

EXAMPLE 5

17α,21-DIESTERS OF 16α AND 16β-METHYL-9α-CHLORO-21-PREDNISOLONES

Stage b of Example 4 is repeated, but carrying out the precipitation in an inverse order, as follows: Once the reflux is finished, the reaction misture is cooled down to 50° C. and 80 ml of water is added to the reaction mixture in order to dissolve the inorganic salts. Subsequently, 1300 ml of water is added dropwise, under stirring, which takes about 4 hours. The precipitate is then filtered and dried, yielding 17.4 g of 16β-methyl-9α-chloro-11β,17α,21-trihydroxy-1,4-pregnadiene-3,20-dione 17α-valerate 21-acetate. The 21-acetate thus obtained is recrystallized from acetone. Melting point 200°–205° C. $E_1^{1\%}{}_{cm}$ 288 at 234 m$\mu$./$\alpha/_D{}^{22}$ +75 (c=1, in dioxan). It is soluble in methanol and chloroform, fairly soluble in acetone and insoluble in water. The main peaks of the infrared absorption in mineral oil mull are at 2.95 $\mu$, 5.7 $\mu$, 5.8 $\mu$, 6.02 $\mu$, 6.2 $\mu$, 6.24 $\mu$, 8.0 $\mu$, 8.12 $\mu$, 11.9 $\mu$, 11.32 $\mu$.

EXAMPLE 6

17α,21-DIESTERS OF 16α AND 16β-METHYL-9α-FLUORO-21-DESOXYPREDNISOLONE

Stage a — 21 g of 11β-trifluoroacetate, obtained in stage b of Example 3, is diiodinated as in stage a and acetoxylated as in stage b of Example 4, yielding 20.8 g of 16β-methyl-9α-fluoro-11β,17α,21-trihydroxy-1,4-pregnadiene-3,20-dione 11β-trifluoroacetate 17α-valerate 21-acetate. Melting range 135°–138° C. $E_1^{1\%}{}_{cm}$ 223 at 237 m$\mu$. The main peaks of the infrared absorption in mineral oil mull are at 5.59 $\mu$, 5.69°–5.75 $\mu$ (doublet), 5.98 $\mu$, 6.1 $\mu$, 6.15 $\mu$, 8.1 $\mu$, 10.25 $\mu$, 11.0 $\mu$, 11.27 $\mu$.

In an analogous manner, the following 17α,21-diesters are prepared through the respective 11β-trifluoroacetates:

16α or 16β-methyl-9α-fluoroprednisolone:
  17α,21-diacetate

17α,21-dipropionate
17α,21-divalerate
17α,21-diheptanoate
17α,21-dicaprylate
17α,21-dipalmitate
17α-propionate 21-acetate
17α-valerate 21-acetate
17α-propionate 21-trimethylacetate
17α-propionate 21-phosphate Stage b — 1 g of the product obtained in the previous stage is solvolysed with silica gel as in stage c of Example 2, yielding 0.77 g of 16β-methyl-9α-fluoro-11β,17α,21-trihydroxy-1,4-pregnadiene-3,20-dione 17α-valerate 21-acetate. Melting point 196°–202° C. $E_1^{1\%}{}_{cm}$ 302 at 239 mμ. The main peaks of the infrared absorption in mineral oil mull are at 2.92 μ, 5.69–5.78 μ (doublet), 6.0 μ, 6.15–6.21 μ, 8.1 μ, 9.4 μ, 11.06 μ, 11.2 μ.

EXAMPLE 7

17α,21-DIESTERS OF 16α AND 16β-METHYL-9α-CHLORO OR 9α-FLUOROPREDNISOLONE FROM 17α-MONOESTERS OF THE RESPECTIVE 21-DESOXYPREDNISOLONES 21 g of the product obtained in stage d of Example 2, is reacted as described in stages a and b of Example 4, yielding 19.3 g of 16β-methyl-9α-chloro-11β,17α,21-trihydroxy-1,4-pregnadiene-3,20-dione 11β-propionate 17α-valerate 21-acetate.

EXAMPLE 8

17α,21-DIESTERS OF 16α AND 16β-METHYL-9α-CHLORO OR 9α-FLUOROPREDNISOLONE BY SOLVOLYSIS OF THE RESPECTIVE 11β-TRIFLUOROACETATES

Stage a — To 20 g of 16β-methyl-9α-fluoro-11β,17α,21-trihydroxy-1,4-pregnadiene-3,20-dione 11β-trifluoroacetate 17α-valerate 21-acetate, obtained in stage a of Example 6, in 3500 ml of methanol, is added 140 ml of 70% perchloric acid. After standing overnight at room temperature, it is precipitated by adding 14 liters of water, yielding 14.1 g of the crude 11β-trifluoroacetate 17α-valerate of betamethasone. Melting point 135°–138° C. $E_1^{1\%}{}_{cm}$ 247 at 237 mμ in methanol. The main peaks of the infrared absorption in mineral oil mull are at 2.9 μ, 5.58 μ, 5.77 μ, 5.98 μ, 6.1–6.2 μ, 8.55 μ, 11.0 μ, 11.24 μ.

Stage b — 1 g of the product obtained in the previous stage is solvolysed with silica gel according to stage c of Example 2, yielding betamethasone 17α-valerate. After recrystallization from acetone and hexane, the analytical values of the product are as described in the literature. Yield 93%.

EXAMPLE 9

11β,17α,21-TRIESTERS AND 11β,21-DIESTERS OF 16α AND 16β-METHYL-9α-CHLORO-PREDNISOLONE

Stage a — 21 g of 16β-methyl-9α-chloro-11β,17α-dihydroxy-1,4-pregnadiene-3,20-dione 11β-propionate 17α-valerate, obtained in stage d of Example 2, is iodinated and 21-acetoxylated as in stages a and b of Example 4, yielding the 11β-propionate 17α-valerate 21-acetate.

In an analogous manner, the following triesters are obtained:
16α or 16β-methyl-9α-chloro-prednisolone:
11β,21-diacetate 17α-propionate
11β,17α-dipropionate 21-acetate
11β,17α,21-tripropionate
11β-propionate 17α-valerate 21-acetate
11β-17α-divalerate 21-acetate Stage b — Example 8 is repeated, but using the triesters obtained in the previous stage instead of the 11β-trifluoroacetate 17α-valerate 21-acetate..

The solvolysis yields the respective 11β,17α-diesters:
11β-acetate 17α-propionate
11β,17α-dipropionate
11β-propionate 17α-valerate
11β,17α-divalerate

EXAMPLE 10

11β, 17α,21-TRIESTERS AND 11β,21-DIESTERS OF 16α and 16β-METHYL-9α-FLUOROPREDNISOLONE Example 4 (stages a and b) is repeated but starting with the 11β,17α-diesters of 16α or 16β-methyl-9α-fluoro-21-desoxyprednisolone, obtained according to stage d of Example 3, yielding:
16α or 16β-methyl-9α-fluoroprednisolone:
11β,21-diacetate 17α-propionate
11β,17α-dipropionate 21-acetate
11β,17α,21-tripropionate
11βpropionate 17α-valerate 21-acetate
11β,17α-valerate 21-acetate
11β-acetate 17α-propionate
11β,17α-dipropionate
11β-propionate 17α-valerate
11β, 17α-divalerate
11β-propionate 17α-heptanoate
11β-butyrate 17α-heptanoate
11β-propionate 17α-caprylate
11β-propionate 17α-palmitate

EXAMPLE 11

PROTECTION OF THE 11β-HYDROXY GROUP BY TETRAHYDROPYRANYL GROUP AND PREPARATION OF 11β AND 17α-MONOESTERS AND 11β,17α-DIESTERS OF 16α OR 16β-METHYL-9α-CHLORO OR 9α-FLUORO-21-DESOXYPREDNISOLONES

Stage a — 1 g of 16β-methyl-9α-chloro-11β,17-dihydroxy-1,4-pregnadiene-3,20-dione is dissolved in 6 ml of 2,3-dihydropyran, and 2 ml of dimethylformamide and 0.1 ml of phosphorous oxychloride are added. The reaction mixture is heated to 35°–40° C., under stirring, for 18 hours. It is then cooled down to 20° C., 25 ml of chloroform is added and the reaction mixture is washed twice with 30 ml of a 10% aqueous solution of sodium bicarbonate. The organic phases are then washed with water. The organic phase is dried with sodium sulfate, and concentrated under vacuum, yielding on oil. It is recrystallized from isopropyl ether and hexane, yielding 16β-methyl-9α-chloro-11β-(tetrahydropyran-2'yloxy)-17α-hydroxy-1,4-pregnadiene-3,20-dione, which is pure enough to be used in the next stage. The main peaks of the infrared absorption in mineral oil mull are at 2.92 μ, 5.82 μ, 6.0 μ, 6.13μ, 6.21 μ, 9.60 μ, 10.90 μ, 11.22 μ, 11.45 μ, 12.24 μ. 100 mg of this compound is dissolved in 1 ml of propionic acid. Upon standing at room temperature it starts to crystallize. At the end of 15 hours, the addition of water completes the crystallization. The product thus obtained is purified but no cleavage takes place at the 11β-position. $E_1$ $_{cm}^{1\%}$ 319 at 239 ±1 mμ in methanol.

Stage b — 20 g of the product obtained according to the previous stage is esterified at the 17α-hydroxy group, using the process described in stage b of Example 2, yielding 14.7 g of 16β-methyl-9α-chloro-21-desoxyprednisolone 17α-valerate.

EXAMPLE 12

1 g of the product obtained in stage a of Example 11 is heated to 100° C. in 10 ml of propionic acid for 2.5 hours. After cooling to 20° C., it is poured into 100 ml of water and ice, yielding 0.8 g of 16β-methyl-9α-chloro-21-desoxyprednisolone 11β-propionate. The main peaks of the infrared absorption in mineral oil mull are at 2.9 μ, 5.81 μ, 5.99 μ, 6.12 μ, 6.21 μ, 9.54 μ, 9.93 μ, 10.54 μ, 11.28 μ. Melting range 228°–231° C. with decomposition.

EXAMPLE 13

Stage a — 10 g of 16β-methyl-9α-fluoro-21-desoxyprednisolone is suspended in 60 ml of 2,3-dihydropyran and 1 ml of phosphorous oxychloride is added. The addition of 20 ml of dimethylformamide provokes complete dissolution. After stirring for 20 hours at room temperature, 250 ml of chloroform is added and the reaction mixture is washed twice with 300 ml of a 5% sodium bicarbonate solution and then with water. The organic phase is then dried with anhydrous sodium sulfate, filtered and evaporated to dryness under reduced pressure, yielding an oil, which is dissolved in 30 ml of ethanol. Upon the addition of 1000 ml of water, an amorphous mass is deposited and the water is decanted. The mass is then dissolved in isopropyl ether and the desired product crystallizes by the addition of hexane, yielding a first crop of 9.8 g. The main peaks of the infrared absorption in mineral oil mull are at 292 μ, 5.82 μ, 6.0 μ, 6.14 μ, 6.21 μ, 9.70 μ, 10.99 μ, 11.21 μ.

Stage b — 9 g of the 9α-fluoro compound obtained in the previous stage is added to a mixture of 60 ml of methanol and 80 ml of tetrahydrofuran. Subsequently, 10 g of calcium oxide and 10 g of iodine are added, portionwise, to the reaction mixture. It is stirred for 1.5 hours at room temperature and then poured into a mixture of 4 liters of water and ice containing 30 ml of acetic acid. The precipitate is washed and dried at 35+ C., yielding 12 g of 16β-methyl-9α-fluoro-11β-(tetrahydropyran-2'-yloxy)-17α-hydroxy-21-iodo-1,4-pregnadiene-3,20-dione. The 21-monoiodo derivative thus obtained is refluxed in 300 ml of acetone and 80 ml of dimethylformamide containing 4.5 g of potassium acetate, for 3 hours. It is then cooled down to 10° C. and 60 g of ice is added, which dissolves the inorganic salts. Precipitation with 3 liters of water and ice yields 7.8 g of the corresponding 21acetate.

Stage c — The product obtained in the previous stage is heated to 100° C. in 80 ml of propionic acid for 2.5 hours. It is cooled to 10° C. and precipitated with 1 liter of water and ice, yielding 7.4 g of 16β-methyl-9α-fluoro-11β,17α,21trihydroxy-1,4-pregnadiene-3,20-dione 11β-propionate 21acetate.

Stage d — The product obtained in the previous stage is added to 1400 ml of benzene, 250 ml of propionic anhydride and 0.25 ml of perchloric acid (70%). It is stirred overnight and then washed three times with 750 ml of 5% sodium bicarbonate and then with water. The organic phase is subsequently dried with anhydrous magnesium sulfate and filtered. The benzene is then evaporated under reduced pressure and the oily product thus obtained is dissolved in methanol and precipitated with water. Subsequently, the crude product is recrystallized from acetone and water to yield the corresponding 11β,17α-dipropionate 21-acetate. The main peaks of the infrared absorption in mineral oil mull are at 5.7 μ(shoulder), 5.78 μ(broad), 6.0 μ, 6.12 μ, 6.21 μ(shoulder), 8.1 μ, 8.5 μ, 9.4 μ, 11.1–11.5 μ. There is no peak in the region at 2.5–3.0 μ.

EXAMPLE 14

Stage d of the previous Example is repeated but replacing the propionic acid with an equal amount of n-valeric acid, the reaction time being 40 hours. It yields 6.78 g of 16β-methyl-9α-fluoro-11β,17α,21-trihydroxy-1,4-pregnadiene3,20-dione 11β-propionate 17α-valerate 21-acetate.

EXAMPLE 15

The compounds obtained in the present invention were tested according to McKenzie's vasoconstriction test (A. W. McKenzie and R. M. Atkinson, Arch. of Derma., Vol. 80, 741–746, 1964). Thirty-four healthy subjects took part in the main experiment. The doses applied were 0.0125, 0.025, 0.05 and 0.1 ug. Three dosages were chosen for each compound (0.0125–0.05 or 0.025–0.1 ug), according estimates based on the preliminary results. Each dose was repeated at least six times, i.e., at least 18 applications per compound were made, while the application with betamethasone 17-valerate, used as standard, was repeated 68 times at four dosage levels.

With a view to facilitating comparison with McKenzie's results, the values for betamethasone valerate were taken as 360, i.e., the potency was expressed in relation to fluocinolone acetonide taken as 100, the results being summarized in the Table below.

In the 21-desoxy series, the 17α-valerate of the 9α-fluoro compound is more potent than the 17α-butyrate, while the 17α-propionate of the 9α-chloro compound is much more potent than the 17α-valerate. Surprisingly, in the 21-desoxy series, the 11β-monoester, 11β,17α-diester and the 11β-(tetrahydropyran-2'-yloxy)-ether are not only highly potent, and with the exception of one, all are also more potent than betamethasone 17-valerate in this test, despite the fact that their systemic activity is considerably lower.

| Compound | Relative Potency (Fluocinolone Acetonide = 100) |
| --- | --- |
| 16β-methyl-9α-chloro-21-desoxyprednisolone 17α-propionate | 422 |
| 16β-methyl-9α-chloro-21-desoxyprednisolone 17α-valerate | 180 |
| 16β-methyl-9α-fluoro-21-desoxyprednisolone 17α-butyrate | 212 |
| 16β-methyl-9α-fluoro-21-desoxyprednisolone 17α-valerate | 540 |
| 16β-methyl-9α-chloro-11β-(tetrahydropyran-2'yloxy)-21-desoxyprednisolone | 296 |
| 16β-methyl-9α-fluoro-11β-(tetrahydropyran-2'yloxy)-21-desoxyprednisolone | 722 |
| 16β-methyl-9α-chloro-21-desoxyprednisolone 11β-propionate | 448 |
| 16β-methyl-9α-fluoro-21-desoxyprednisolone 11β-propionate 17α-valerate | 705 |
| 16β-methyl-9α-chloro-prednisolone 17α-valerate | 90 |
| 16β-methyl-9α-fluoro-prednisolone 17α-valerate | 360 |

-continued

| Compound | Relative Potency (Fluocinolone Acetonide = 100) |
|---|---|
| 16α-methyl-9α-fluoro-prednisolone 17α-valerate | 280 |
| 16β-methyl-9α-chloro-prednisolone 17α-valerate 21-acetate | 450 |
| 16β-methyl-9α-fluoro-prednisolone 17α-valerate 21-acetate | 186 |
| 16α-methyl-9-α-fluoro-prednisolone 17α-valerate 21-acetate | <50 |
| 16β-methyl-9α-fluoro-prednisolone 11β,17α-dipropionate 21-acetate | 470 |

Every clearly visible white aureola or patch was considered positive. After 15 hours, the occlusive polyethylene tubing was removed and the observations were made after 0.25, 1, 2, 3, 4 and 5 hours. It is noteworthy to mention that in all cases the maximum visibility of the positive reaction was between 0.25 and 3 hours, whereas for the triester all patches appeared only after 3 hours or their intensity increased until the 4th hour.

The 16α-methyl series are clearly inferior to the 16β-methyl isomers in this test, suggesting that the steric configuration of the 16-methyl group has a significant role in the action mechanism of the steroids in this test.

The Examples appearing hereinafter illustrate the preparation of pharmaceutical compositions, in accordance with the invention (all percentage is expressed in weight/weight):

A - TABLETS

| Each tablet contains | |
|---|---|
| 16β-methyl-9α-fluoro-prednisolone 17α-heptanoate | 1 mg |
| Lactose | 70 mg |
| Starch | 28 mg |
| Magnesium stearate (100 mesh) | 1 mg |
| | 100 mg |

B - INTRAMUSCULAR INJECTION

| 16β-methyl-9α-fluoro-prednisolone 17α-caprylate (sterile) | 10 mg |
|---|---|
| Seasan oil (sterile) per ampoule. | 1 ml |

The intramuscular administration provokes effective maintenance levels of the steroid for about 8 days.

C - OINTMENT

| 16β-methyl-9α-fluoro-21-desoxyprednisolone 17α-valerate | 0.025–0.1% |
|---|---|
| Liquid paraffin | 10% |
| White soft paraffin q.b ad | 100% |

Ball mill the steroid with a small amount of liquid paraffin. Dilute the paste and rinse out the mill with the remaining liquid paraffin, mix and add it to the melted soft paraffin at around 50° C. Stir until homogenity and fill in.

D - WATER MISCIBLE CREAM

| 16β-methyl-9α-chloro-21-desoxyprednisolone 17α-valerate | 0.025–0.1% |
|---|---|
| Beeswax | 15% |
| Polyethylene glycol 1000 monocetyl ether | 3% |
| Cetostearyl alcohol | 7% |
| Liquid paraffin (high viscosity) | 4% |
| Propyleneglycol | 1% |
| p-hydroxymethyl benzoate | 0.07% |
| p-hydroxypropyl benzoate | 0.03% |
| Distilled water q.b. ad | 100% |

Ball mill the 16β-methyl-9α-chloro-21-desoxyprednisolone 17α-valerate with a small amount of paraffin as above. Dissolve separately the hydroxy benzoates, stir in water at 100° C. and cool down to 65° C. Separately, melt together the beeswax, cetostearyl alcohol and polyethylene glycol 1000 monocetyl ether and maintain the mixture at 65° C. Add the steroid suspension, heated to 65° C., to the second melting, using the remaining liquid paraffin and propylene glycol for rinsing. Add finally this mixture at 60° C. to the aqueous solution of the hydroxy benzoates at 65° C., under rapid stirring until gelling (ca. 40° C.), and let the emulsion cool down completely under slow stirring.

This cream is for dermatological use. The rectal cream for the treatment of hemorrhoids is prepared in the same way but the concentration of the steroid is 0.25%. For the treatment of infected areas, 0.6% of neomycin sulfate or 0.1% of iodochlorohydroxyquin is also incorporated into the ointment or cream.

A prolonged treatment, three to four times a day, does not decrease the natural cortisol levels in the plasma, thus its application, even prolonged, does not depress the normal function of the suprarenal glands.

E - LOTION

| 16β-methyl-9α-fluoro-prednisolone 11β,17α-dipropionate 21-acetate | 0.025–0.1% |
|---|---|
| Liquid paraffin | 10% |
| Alcohol | 2% |
| Glycerin | 1.5% |
| Propylene glycol | 2.5% |
| Polyethylene 1000 monocetyl ether | 1.5% |
| Non-ionic emulsifier | 0.5% |
| Water q.b. ad | 100% |

Various changes and modifications can be made in the process and products of this invention without departing from the spirit and the scope thereof. The various embodiments set forth herein were presented for the purpose of further illustrating the invention and were not intended as limiting.

What is claimed is:

1. A process for the preparation of 16-methyl-9α-chloro or fluoro steriod compounds of high topical and/or protracted activity of the formula

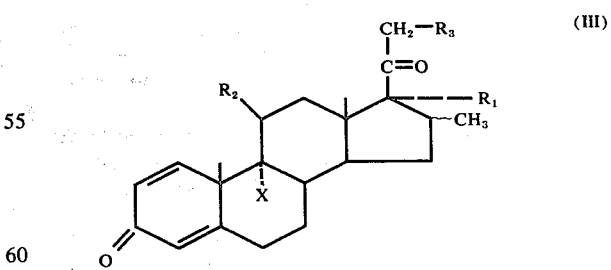

wherein X is chlorine or fluorine, $R_1$ and $R_2$ are hydroxyl or esterified hydroxyl provided at least one of $R_1$ and $R_2$ is esterified hydroxyl, $R_3$ is hydrogen, hydroxy or an esterified hydroxy group, comprising (A) selectively protecting the 11β-hydroxy of a compound of the formula

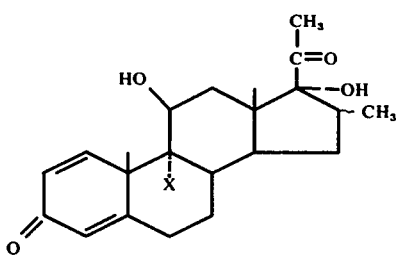

wherein X is chlorine or fluorine, with a tetrahydropropyranyl group to obtain a compound of the formula

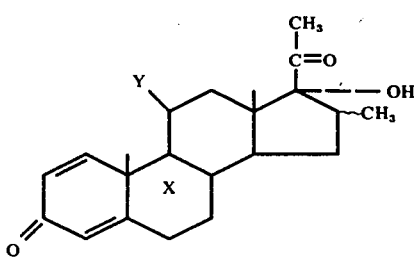

wherein Y is said tetrahydropyanyl group; and therafter (B) esterifying the 17α-hydroxyl group; whereby an 11α-protected 17α-monoester is obtained.

2. The process of claim 1 wherein said tetrahydropyanyl group of the 17α- esterified steroid produced in step (B) is removed by hydrolysis, 3. The process of claim 2 wherein the hydrolyzed steroid is esterified at 11α, whereby an 11α,17α-diester is obtained.

4. The process of claim 2 wherein the 21 group of the 11α,17α-diester whereby an 11β,17α,21-triester is obtained.

5. The process of claim 2 wherein said hydrolozyed steroid is esterified at the 11β-position by contact with an excess of a 1–16 carbon atom carboxylic acid or anhydride thereof in the presence of an acid catalyst.

6. The process of claim 2 wherein said tetrahydropyranyl and group is removed by contact with (a) ethanol or ethanol containing para-toluenesulfonic acid, dilute aqueous organic acid, aqueous magnesium sulfate, or silica gel.

7. The process of claim 1 wherein the 21 group is acyloxylated subsequent to step (B) whereby an 11β-tetrahydropyanyl 17α,21-diester is obtained.

8. The process of claim 7 wherein said tetrahydropyanyl group of the 17α- esterified steroid produced in step (B) is removed by hydrolysis, whereby an 11β-hydroxy 17α,21-diester is obtained.

9. The process of claim 7 wherein the 21-ester group is converted to a hydroxyl group by weak akaline hydrolysis, whereby a 21-hydroxy, 11β-tetrahydropyanyl 17α-ester is obtained.

10. The process of claim 9 wherein the 11β-tetrahydropyanyl group is converted into a hydroxyl group by a solvolysis, whereby an 11β,21-dihydroxy 17α-ester is obtained.

11. The process of claim 7 wherein said 11β-tetrahydropyranyl 17α,21-diester is heated in a lower carboxylic acid to convert said tetrahydropyranyl group into an ester group, whereby an 11β17α,21-triester is obtained.

12. The process of claim 7 wherein said tetrahydropyranyl group is cleaved from said 11β-protected 21-esterified hydroxy, 17α-monoester by solvolysis, whereby an 11β,21-dihydroxy 17α-monoester is obtained.

13. The process of claim 9 wherein the conversion of the 21-ester group to a hydroxyl group is effected by contacting the 11β-tetrahydropyranyl 17α,21-diester with methanol or ethanol containing perchloric acid or aqueous sodium bicarbonate.

14. The process of claim 1 wherein step (A) is effected by contacting said compound of formula IV with an excess of 2,3-dihydropyran in the presence of an acid catalyst, at 0°–80° C. for 1–40 hours.

15. The process of claim 1 wherein step (B) is effected by contacting said compound of formula V with an excess of a 1–16 carbon atom carboxylic acid or anhydride thereof in the presence of an acid catalyst.

16. The process of claim 1 wherein $R_1$ is an esterified hydroxyl group of 1–16 carbon atoms, $R_2$ is hydroxy or an esterified hydroxyl group of 1–8 carbon atoms or a tetrahydropyran-2'-yloxy group, $R_3$ is hydrogen and X is chlorine.

17. The process of claim 1 wherein $R_1$ is an esterified hydroxyl group of 5–16 carbon atoms, $R_t$ is hydroxy or an esterified hydroxyl group of 1–8 carbon atoms or a tetrahydropyran-2'-yloxy group, $R_3$ is hydrogen and X is fluorine.

18. A process for the preparation of a 16-methyl-9α-chloro or fluoro steroid 11β-monoester of high topical and/or protracted activity of the formula

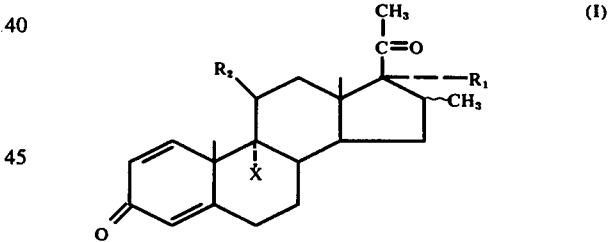

wherein X is chlorine or fluorine, $R_1$ is hydroxyl, and $R_2$ is an esterified hydroxyl group comprising selectively protecting the 11β-hydroxyl of a compound of the formula

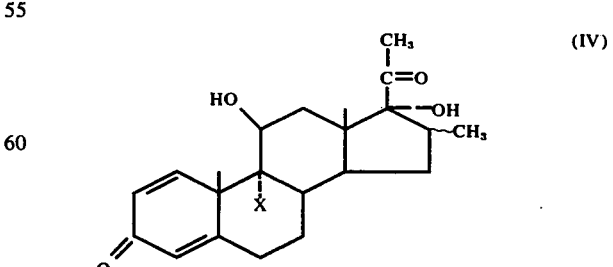

wherein X is chloro or fluoro with a a tetrahydropyranyl to obtain a compound of the formula

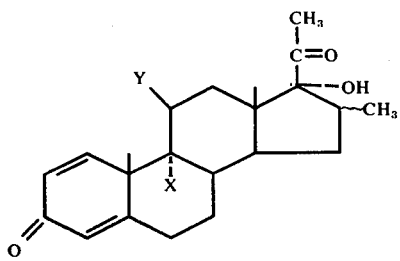

(V)

wherein Y is said tetrahydropyranyl group, and thereafter heating said protected steroid in a lower carboxylic acid.

19. A process for the preparation of 16-methyl-9α-chloro or fluoro steroid compounds of high topical and/or protracted activity of the formula

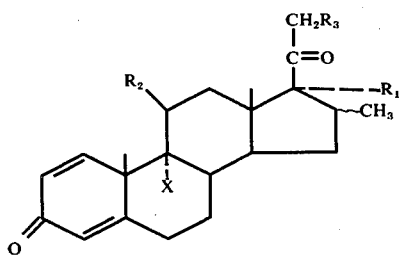

wherein X is chlorine or fluorine, $R_1$ and $R_2$ are hydroxyl or esterified hydroxyl provided at least one of $R_1$ and $R_2$ is esterified hydroxyl, $R_3$ is hydrogen, hydroxy or an esterified hydroxy group, comprising (A) selectively protecting the 11β-hydroxy of a compound of the formula

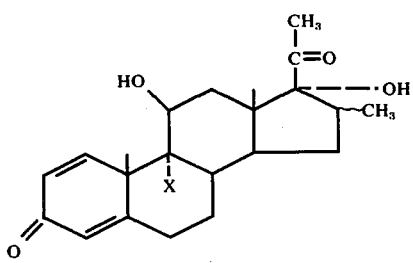

wherein X is chlorine or fluorine or fluorine, with a di, trichloro or fluoroacetyl group or tetrahydropyranyl group to obtain a compound of the formula

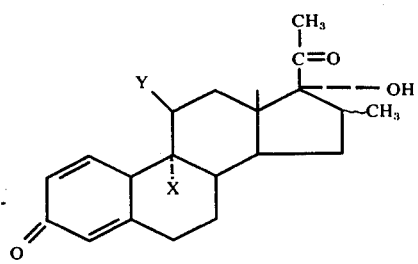

wherein Y is said protecting group; (B) esterifying the 17α-hydroxyl group, whereby an 11β-protected 17α-monoester is obtained: (C) removing said protecting group of the 17α-esterified steroid produced in step (B) by hydrolysis; (D) esterifying the hydrolyzed steroid at 11β, whereby an 11β, 17α-diester is obtained; and (E) contacting the 11β, 17α-diester with iodine in the presence of calcium oxide or calcium chloride and the 21 -oido derivative thus obtained is reacted with a salt of a carboxylic acid, phosphoric acid or sulfuric acid.

20. A process for the preparation of 16-methyl-9α-chloro or fluoro steroid compounds of high topical and/or protracted activity of the formula

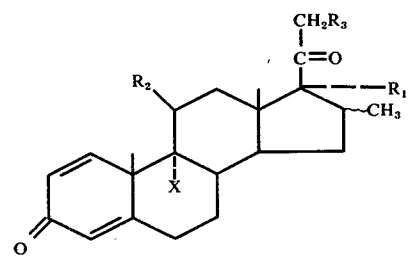

wherein X is chlorine or fluorine, $R_1$ and $R_2$ are hydroxyl or esterified hydroxyl provided at least one of $R_1$ and $R_2$ is esterified hydroxyl, $R_3$ is hydrogen, hydroxy or an esterified hydroxy group, comprising (A) selectively protecting the 11β-hydroxy of a compound of the formula

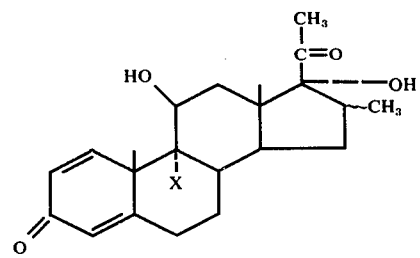

wherein x is chlorine or fluorine, with a di, trichloro or fluoroacetyl group to obtain a compound of the formula

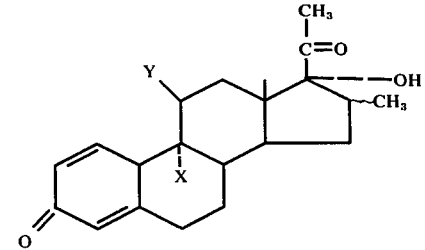

wherein Y is said protecting group; (B) esterifying the 17α-hydroxyl group, whereby an 11β-protected 17α-monoester is obtained; and (C) removing said protecting group by (a) contact with activated silica gel employing as the solvent, a member of the group consisting of dichloromethane, trichloromethane, tetrachloromethane, tetrahydrofuran, dioxane, benzene, ethylacetate and mixtures thereof, or (b) contact with an aqueous sodium bicarbonate solution and methanol.

21. A process for the preparation of 16-methyl-9α-chloro or fluoro steroid compounds of high topical and/or protracted activity of the formula

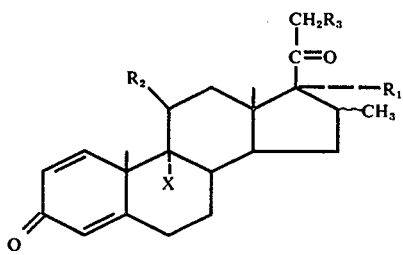

wherein X is chlorine or fluorine, R₁ and R₂ are hydroxyl or esterified hydroxyl provided at least one or R₁ and R₂ is esterified hydroxyl, R₃ is hydrogen, hydroxy or an esterified hydroxy group, comprising (A) selectively protecting the 11β-hydroxy of a compound of the formula

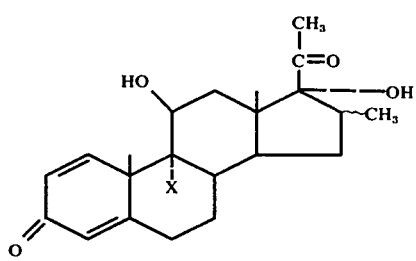

wherein X is chlorine or fluorine, with a di, trichloro or fluoroacetyl group or tetrahydropyranyl group to obtain a compound of the formula

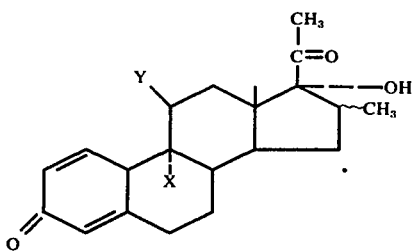

wherein Y is said protecting group; (B) esterifying the 17α-hydroxyl group, whereby an 11β-protected 17α-monoester is obtained; (C) introducing an esterified hydroxyl group at 21 by contacting the 11β-protected 17α-monoester with iodine in the presence of calcium oxide or calcium chloride, and the 21-iodo derivative thus obtained is contacted with a salt of a carboxylic acid, phosphoric acid or sulphuric acid; and (D) removing said protecting group by hydrolysis whereby an 1β-hydroxy 17α,21-diester is obtained.

22. A process for the preparation of 16-methyl-9α-chloro or fluoro steroid compounds of high topical and/or protracted activity of the formula

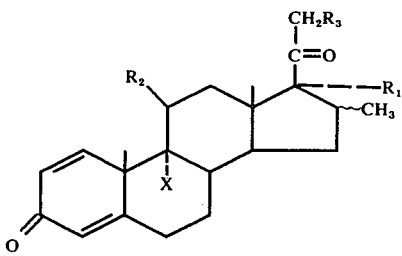

wherein X is chlorine or fluorine, R₁ and R₂ are hydroxyl or esterified hydroxyl provided at least one of R₁ and R₂ is esterified hydroxyl, R₃ is hydrogen, hydroxy or an esterified hydroxy group, comprising (A) selectively protecting the 11β-hydroxy of a compound of the formula

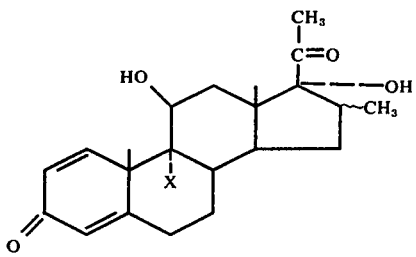

wherein X is chlorine or fluorine, with a di, trichloro or fluoroacetyl group to obtain a compound of the formula

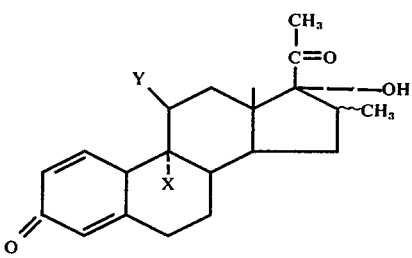

wherein Y is said protecting group (B) esterifying the 17α-hydroxyl group, whereby an 11β-protected 17α-monoester is obtained: (2) acyloxylating the 11β-protected 17α-monoester at 21 whereby an 11β-protected 17α,21-diester is obtained; (D) converting the 21-ester group to a hydroxy group by weak alkaline hydrolysis, whereby a 21-hydroxy, 11β-protected, 17α-ester is obtained; and (E) converting the 11β-halocetyl group into a hydroxyl group by contact with activated silica gel, whereby an 11β,21-dihydroxy 17α-ester is obtained.

23. A process for the preparation of 16-methyl-9α-chloro or fluoro steroid compounds of high topical and/or protracted activity of the formula

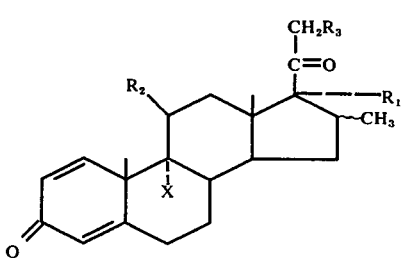

wherein X is chlorine or fluorine, R₁ and R₂ are hydroxyl or esterified hydroxyl provided at least one of R₁ and R₂ is esterified hydroxyl, R₃ is hydrogen, hydroxy or an esterified hydroxy group, comprising (A) selectively protecting the 11β-hydroxy of a compound of the formula

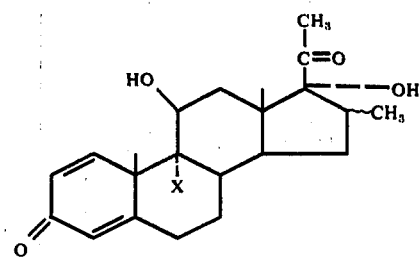

wherein X is chlorine or fluorine, with a di, trichloro or fluoroacetyl group of tetrahydropyranyl group to obtain a compound of the formula

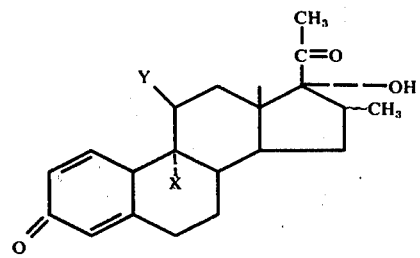

wherein Y is said protecting group; (B) esterifying the 17α-hydroxyl group, whereby an 11β-protected 17α-monoester is obtained; (C) contacting the 1β-protected 17α-monoester with iodine in the presence of calcium chloride in methanol, whereby the 2t-monoiodo and 2-diiodo derivatives are obtained; (D) contacting the 21-iodo derivatives with a salt of a carboxylic acid, phosphoric acid or sulfuric acid, whereby a 21-esterified compound by pouring the reaction mixture rapidly into iced water.

24. A process for the preparation of 16-methyl-9α-chloro or fluoro steroid compounds of high topical and/or protracted activity of the formula

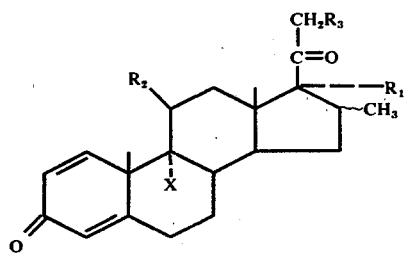

wherein X is chlorine or fluorine, $R_1$ and $R_2$ are hydroxyl or esterified hydroxyl provided at least one of $R_1$ and $R_2$ is esterified hydroxyl, $R_3$ is hydrogen, hydroxy or an esterified hydroxy group, comprising (A) selectively protecting the 11β-hydroxy of a compound of the formula

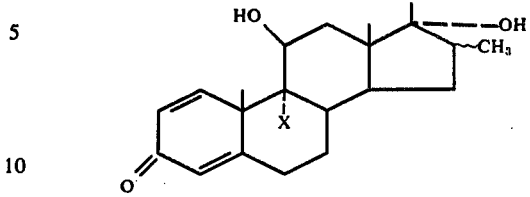

wherein X is chlorine or fluorine, with a di, trichloro or fluoroacetyl group of tetrahydropyranyl group to obtain a compound of the formula

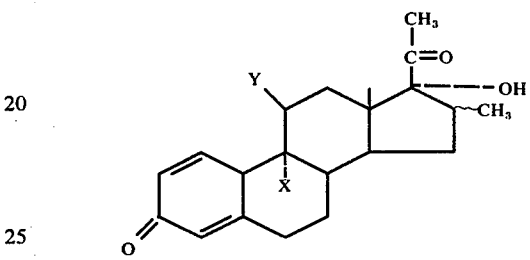

wherein Y is said protecting group; (B) esterifying the 17α-hydroxyl group, whereby an 11β-protected 17α-monoester is obtained; (C) contacting the 11β-protected 17α-monoester with iodine in the presence of calcium oxide or calcium chloride whereby the 21-iodo derivative is obtained; (D) contacting the 21-iodo derivative with a salt of a carboxylic acid, phosphoric acid or sulfuric acid, whereby a 21-esterified compound is obtained; and (E) precipitating the resulting 2-esterified compound by slowly adding water to the reaction mixture.

25. The process of claim 1 wherein the 11β-tetrahydropyranyl 17α-monoester is contacted with iodine in the presence of calcium chloride in methanol; the 21-monoiodo and 21-diiodo derivatives thus obtained are contacted with a salt of a carboxylic acid, phosphoric acid or sulfuric acid; the resultant 21-esterified compound is precipitated by pouring the reaction mixture rapidly into iced water; and wherein the 11β-tetrahydropyranyl group is removed from the 11β-tetrahydropyranyl 17α,21-di-ester by contact with activated silica gel employing as the solvent a member of the group consisting of dichloromethane, trichloromethane, tetrachloromethane, tetrahydrofuran, dioxane, benzene, ethyl acetate and mixtures thereof.

26. 16-methyl-9α-fluoro-21-desoxyprednisolone 11β-propionate,17α-valerate.

27. 16β-methy-9α-fluoro-prednisolone 11β, 17α-dipropionate, 21-acetate.

28. 16-methyl-9α-halo-11β-(tetrahydropyran-2′-yloxy)-21-desoxyprednisolone, wherein halo is fluoro or chloro.

29. 16-methyl-9α-halo-11β-(tetrahydropyran-2′-yloxy)-prednisolone wherein halo is fluoro or chloro.

30. An ester of 16-methyl-9α-chloro-11β(tetrahydropyran-2′-yloxy) prednisolone selected from the group consisting of 17-propionate, 17-valerate, 17,21-dipropionate and 17,21-divalerate.

* * * * *

UNITED STATES PATENT OFFICE

CERTIFICATE OF CORRECTION

Patent No. 4,024,131                    Dated May 17, 1977

Inventor(s) Joao Emerico Villax

It is certified that error appears in the above-identified patent and that said Letters Patent are hereby corrected as shown below:

Under "Foreign Application Priority Data" additionally read -- Mar. 10, 1975 Portugal . . . 61636 (ADD'N) --.

Column 6, line 45, for "mole" read -- mol --.

Column 7, line 30, for "maybe" read -- may be --.

Column 8, line 10, for "prepared" read -- prepare --;
line 11, after "using" read -- as --;
line 28, for "9$\beta$" read -- 9$\alpha$ --.

Column 9, line 39, for "C," read -- C. --;
line 40, for "than" read -- then --.

Column 12, line 13, for "obtaines" read -- obtains --;
line 19, for "16$\beta$" (first occurrence read -- 16$\alpha$ --;
line 61, for "5.69°" read -- 5.69 --.

Column 14, line 31, for "$\beta$proprionate" read -- $\beta$-proprionate --.

Column 15, line 39, for "292" read -- 2.92 --;
line 48, for "35+" read -- 35° --
line 57, for "21acetate" read -- 21-acetate --;
line 62, for "21trihydroxy" read -- 21-trihydroxy --;
line 63, for "21acetate" read -- 21-acetate --.

UNITED STATES PATENT OFFICE
CERTIFICATE OF CORRECTION

Patent No. 4,024,131　　　　　　Dated May 17, 1977

Inventor(s)　Joao Emerico Villax

It is certified that error appears in the above-identified patent and that said Letters Patent are hereby corrected as shown below:

Column 17, line 56, for "homogenity" read -- homogeneity --.

Column 19, in the formula (V), read dash lines leading to the X in the same manner as in formula (IV) thereabove;

line 27, for "therafter" read -- thereafter --;
        line 30, for "11α-protected" read -- 11β-hydropyranyl --;
        line 33, for "," read -- . --;
        line 35, for "11α" read -- 11β -- in both instances;
        line 37, for "2" read -- 3 --;
        line 38, for "11α, 17α-diester" read -- 11β, 17α-diester is acyloxylated --;
        line 45, delete "and";
        line 57, for "akaline" read -- alkaline --.

Column 22, line 2, for "oido" read -- iodo --.

Column 25, line 32, for "1β" read -- 11β --;
               line 34, for "2t" read -- 21 --;
               line 35, for "2" read -- 21 --;
               line 40, after "compound" read -- is obtained; and (E) precipitating the 21-esterified compound --.

UNITED STATES PATENT OFFICE
CERTIFICATE OF CORRECTION

Patent No. 4,024,131      Dated May 17, 1977

Inventor(s) Joao Emerico Villax

It is certified that error appears in the above-identified patent and that said Letters Patent are hereby corrected as shown below:

Column 26, line 14, for "of" read -- or --;
               line 36, for "2" read -- 21 --; and
               line 53, for "methy" read -- methyl --.

Signed and Sealed this

Thirteenth Day of March 1979

[SEAL]

Attest:

RUTH C. MASON
Attesting Officer

DONALD W. BANNER
Commissioner of Patents and Trademarks